(12) United States Patent
Effing

(10) Patent No.: US 8,118,792 B2
(45) Date of Patent: *Feb. 21, 2012

(54) ANTIMICROBIAL WOUND CONTACT LAYER

(75) Inventor: Jochem Effing, Kelkheim-Fischbach (DE)

(73) Assignee: Paul Hartmann AG, Heidenheim (DE)

( * ) Notice: Subject to any disclaimer, the term of this patent is extended or adjusted under 35 U.S.C. 154(b) by 611 days.

This patent is subject to a terminal disclaimer.

(21) Appl. No.: 12/140,526

(22) Filed: Jun. 17, 2008

(65) Prior Publication Data

US 2008/0249453 A1  Oct. 9, 2008

Related U.S. Application Data

(63) Continuation of application No. PCT/EP2006/012100, filed on Dec. 15, 2006.

(30) Foreign Application Priority Data

Dec. 17, 2005 (DE) .................. 10 2005 060 461

(51) Int. Cl.
*A61F 13/00* (2006.01)

(52) U.S. Cl. ........... 604/304; 602/48; 424/409; 424/618

(58) Field of Classification Search ............. 604/19, 604/27, 46, 48, 289, 304–308, 332, 336; 514/969, 7.6, 16.5, 20.9, 154, 565, 600, 626; 424/141.1, 94.1, 409, 618; 602/41, 48, 58; 428/40.1, 40.2, 40.5, 40.6; 260/17.4 CC See application file for complete search history.

(56) References Cited

U.S. PATENT DOCUMENTS

| 4,503,034 | A | * | 3/1985 | Maupetit et al. | ........... 424/78.05 |
| 7,005,556 | B1 | * | 2/2006 | Becker et al. | ........... 602/48 |
| 2003/0036717 | A1 | | 2/2003 | Apert | |
| 2004/0049145 | A1 | | 3/2004 | Flick | |
| 2005/0142154 | A1 | * | 6/2005 | Blatt et al. | ........... 424/401 |
| 2008/0249453 | A1 | * | 10/2008 | Effing | ........... 602/48 |
| 2008/0249485 | A1 | * | 10/2008 | Effing | ........... 604/304 |
| 2008/0249486 | A1 | * | 10/2008 | Effing | ........... 604/304 |

FOREIGN PATENT DOCUMENTS

| DE | 10 2004 031955 | 1/2006 |
| EP | 65399 A1 | 5/1982 |
| EP | 0 065 399 | 11/1982 |
| EP | 0 107 526 | 5/1984 |
| EP | 0107526 | 5/1984 |
| EP | 0 621 031 | 10/1994 |
| EP | 621031 | 10/1994 |
| EP | 1 159 972 | 12/2001 |

(Continued)

OTHER PUBLICATIONS

International Search Report of PCT/EP2006/012100 Mailed on May 14, 2007 (3 pages).

*Primary Examiner* — Patricia Bianco
*Assistant Examiner* — Benedict L Hanrahan
(74) *Attorney, Agent, or Firm* — Brinks Hofer Gilson & Lione

(57) ABSTRACT

The invention relates to a wound dressing, a wound contact layer and a medicinal composition comprising a hydrophilic base in which hydrocolloids are dispersed, wherein the hydrophilic base comprises at least one emulsifier and the use of said composition for treating wounds.

18 Claims, 1 Drawing Sheet

FOREIGN PATENT DOCUMENTS

Figure 1:
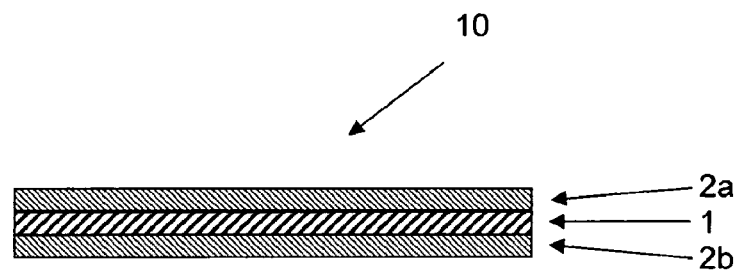

| | | |
|---|---|---|
| JP | 11-319067 | 11/1999 |
| JP | 2003-527212 | 9/2003 |
| JP | 2004-305725 | 11/2004 |
| WO | 96/36315 A | 5/1996 |
| WO | WO 96/36315 | 11/1996 |
| WO | 01/60599 | 8/2001 |
| WO | WO 01/60599 | 8/2001 |
| WO | 01/070285 | 9/2001 |
| WO | WO 01/70285 | 9/2001 |
| WO | 2004/060314 | 7/2004 |
| WO | 2005/065603 | 7/2005 |

\* cited by examiner

ANTIMICROBIAL WOUND CONTACT LAYER

CROSS-REFERENCE TO RELATED APPLICATIONS

This application is a continuation of International Application No. PCT/EP2006/012100 filed on Dec. 15, 2006, which claims the benefit of DE 10 2005 060 461.7, filed Dec. 17, 2005. The disclosures of the above applications are incorporated herein by reference.

FIELD

The invention concerns an antimicrobial wound contact layer as well as its use for wound treatment.

BACKGROUND

The statements in this section merely provide background information related to the present disclosure and may not constitute prior art.

A multitude of ointments and other compositions have been known and utilized in past decades for the treatment of humans. These ointments are usually semisolid compositions which are intended for use on healthy skin or some mucous membranes, for example, on the eyes. A localized effect is usually to be achieved with these ointments or preparations, active ingredients are to be administered percutaneously, or a softening or protective action is to be exerted on the skin.

Numerous ointments for wound care are furthermore known. Thus, for example, EP 621 031 describes a wound ointment, which is formulated as a gel and contains at least one gel-forming polysaccharide and hexylene glycol. Carboxymethyl cellulose or sodium alginate in particular should be used as a gel-forming polysaccharide. This composition should have an antimicrobial action and be non-toxic with respect to fibroplasts.

EP 107 526 also describes a paste, which protects the skin, for example, in wound treatment or stoma care, is formulated as a gel, and contains polyvinyl pyrrolidone, carboxymethyl cellulose, alginate, water, an oil, and a fatty acid ester. This gel contains at least 20% by weight of water and at least 45% by weight of hydrocolloids.

Hydrophilic ointments are furthermore known, which absorb a limited portion of water and can be utilized for wound care. These ointments contain a mixture of various monoglycerides, diglycerides, and triglycerides and nonpolar oil, and are processed, for example, in the Atrauman® products, on substrates for production of so-called ointment dressings.

EP 65 399 discloses, in addition, a sterile wound dressing having a substrate impregnated with a wound ointment and a water-soluble film of polyvinyl pyrrolidone. The ointment can be a hydrophilic or hydrophobic wound ointment.

From WO 96/036 315 is known a sterilizable paste or cream, which contains an emulsion and a water insoluble, gel-forming material, which can be crosslinked carboxymethyl cellulose. The emulsion can, in turn, contain oil or wax, water, and emulsifier, wherein the water content amounts to at least 40% by weight.

WO 01/070 285 discloses a dressing for wound treatment which comprises a hydrophobic elastomer matrix in which hydrocolloid particles are dispersed. The matrix should further contain 55 to 90% of nonpolar oil and a surfactant with an HLB value greater than 10.

SUMMARY

The present disclosure provides a wound contact layer which can absorb the wound exudate produced by a wound and optimally support the healing process of a wound by releasing an active ingredient. In addition, a wound contact layer should be made available which can absorb a wound exudate produced by a wound, dispense an active ingredient, and make available a moist wound healing environment. A wound dressing should also be made available which can be used in particular with moderately to heavily exuding wounds.

In one form, a means of a wound contact layer is provided that contains a) A composition for wound treatment with less than 10% by weight of water, containing 60 to 95% of hydrophilic base, in which 5 to 40% by weight of hydrocolloids are dispersed, wherein the hydrophilic base contains is at least 0.5 to 50% by weight of emulsifier, and b) A substrate containing a metal with antimicrobial action for the composition.

All of the content information is to be understood in connection with the invention herein and below as percentages by weight with respect to the overall weight of the medicinal composition, unless otherwise indicated. A medicinal composition is to be understood in connection with the present invention as a hydrophilic base which is mono- or multiphasic and is made available as an emulsion owing to the presence of at least one emulsifier, or is capable of forming an emulsion. These emulsions can be emulsions containing at least one water and/or gel phase and at least one oil phase.

One advantage of this wound contact layer is that, owing to the content of hydrocolloids which are dispersed in the hydrophilic base, the composition is able to absorb very quickly a particularly large amount of liquids, such as, for example, wound exudate. The hydrophilic base forms an emulsion a very short time after coming in contact with liquids, whereupon, in a second step, the water in the emulsion is absorbed by the hydrocolloids dispersively distributed in the base. This process can also be carried out in parallel. In each case, the hydrocolloids form a second liquid reservoir along with the forming emulsion. By means of the substrate, it is ensured that the wound contact layer is easy to apply and can be applied directly over the entire area of the wound. It can be provided herein that the composition can be coated on at least one side of the substrate or applied in any other way. The composition can also be applied on both sides of the substrate or the substrate can be fully impregnated with the composition. The release of an antimicrobial metal is controlled herein by, among other things, the absorption of wound exudate. The more wound exudate is absorbed by the hydrophilic base or the hydrocolloids, the more antimicrobial metal is released. The substrate layer represents thus a depository for the metal which can be released in a controlled manner by the composition.

In another form of the wound contact layer, the hydrophilic base should contain less than 10% by weight or should rather be anhydrous. This hydrophilic base is thus available as a monophasic mixture, and is able to form an emulsion, when water, for example, is added, owing the presence of at least one emulsifier. Here and below, it is meant in connection with the invention that the hydrophilic base can contain traces of water, while the content of water should be at the most 1% by weight with respect to the weight of the hydrophilic base.

In yet another form, the composition has a hydrophilic base which is a cream, cream base, or ointment. The hydrophilic base is in particular a hydrophilic cream or cream base or a hydrophilic ointment. Under ointment should be understood herein and within the context of this application a monophasic system, whereas a cream is a biphasic or multiphasic system. A precise distinction of these formulations also in delimitation of further formulations is provided by the German Pharmacopeia DAB 9 and its commentary, to which reference is expressly made herein.

The composition can, in addition, also contain a hydrophilic base, which furthermore contains about 10 to about 30% by weight of nonpolar lipids.

Within the scope of the disclosure, the expression "lipid" is used as generic term for fats, oils, waxes, and the like. Also, the concepts "oil phase" and "lipid phase" are used as synonymous. Lipids differ, among other things, in their polarity. It has already been proposed that interfacial surface tension with respect to water be adopted as a measure of the polarity of a lipid or lipid phase. This means that the polarity of the lipid phase in question is greater, the lower the interfacial surface tension between this lipid phase and water. According to the disclosure, the interfacial surface tension is considered as one possible measure of the polarity of a specific oil component. The interfacial surface tension is the force acting on an imaginary line having a length of one meter in the interfacial layer between two phases. The physical unit for this interfacial tension is conventionally calculated from the force/length relationship and is usually expressed in mN/m. It has a positive sign if it has the tendency to reduce the interfacial layer. In the opposite case, it has a negative sign. Lipids are particularly considered to be polar in the sense of the invention when their interfacial surface tension with respect to water is less than 20 mN/m, and are considered to be nonpolar when their interfacial surface tension with respect to water is in particular more than 30 mN/m. Lipids with an interfacial surface tension with respect to water of between 20 and 30 mN/m are generally called semipolar.

Nonpolar lipids are particularly lipids selected from the group of branched and unbranched hydrocarbons and hydrocarbon waxes, in particular petroleum jelly, petrolatum, paraffin oil, mineral oil, and polyisobutene.

Along with nonpolar lipid components, the hydrophilic base according to the invention can also contain polar and semipolar lipids. Polar or semipolar lipids can be, for example, from the group of fatty acid triglycerides, fatty acid diglycerides, fatty acid monoglycerides, or fatty acid esters of oligomeric glycerol, such as, for example full or partial fatty acid esters of diglycerin or triglycerin. Triglycerides, diglycerides, and monoglycerides can be esters of saturated and/or unsaturated, branched and/or unbranched alkane carboxylic acids with a chain length of 8 to 24, in particular 12 to 18 C atoms. The fatty acid triglycerides, fatty acid diglycerides, or fatty acid monoglycerides can be advantageously selected, for example, from the group of synthetic, semisynthetic, and natural fats or oils.

Also considered as hydrophilic base in connection with the invention is a mixture containing a portion of polar and nonpolar lipids and at least 0.5 to 30% by weight of emulsifier, wherein the portion of semipolar and polar lipids in the hydrophilic base is more than 1:1, in particular more than 2:1, with respect to the portion of nonpolar lipids, and very particularly between 3:1 and 10:1 with reference to the overall content of lipids.

A composition according to the disclosure has in particular a hydrophilic base containing about 20-80% by weight of monoglycerides, diglycerides, or triglycerides and/or full or partial esters of oligomeric glycerol with reference to the overall weight of the composition. The hydrophilic base contains in particular about 30-70% by weight and very particularly about 40-70% by weight of monoglycerides, diglycerides and/or triglycerides and/or full or partial esters of oligomeric glycerol with reference to the overall weight of the composition. It is particularly advantageous herein if the composition contains about 10-50% by weight of monoglycerides, diglycerides and/or triglycerides and about 10-30% by weight of partial esters of oligomeric glycerol, in particular of diglycerin or triglycerin.

In another form, a composition according to the invention has a hydrophilic base containing about 40-80% by weight of monoglycerides, diglycerides and triglycerides and/or partial esters of oligomeric glycerol, in particular of diglycerin or triglycerin, about 15-30% by weight of nonpolar fats, and about 0.5-30% by weight of emulsifier with reference to the overall weight of the composition.

As emulsifiers should be understood, in connection with the disclosure, substances having surface active activity, so that when water is added to the hydrophilic base, a multiphasic mixture can be formed, namely an emulsion. A composition according to the invention should contain in particular an emulsifier, by means of which the hydrophilic base is capable of forming, upon addition of water, a water-in-oil emulsion (W/O emulsion), gel-in-oil emulsion (G/O emulsion), an oil-in-water emulsion (O/W emulsion), an oil-in-gel emulsion (O/G emulsion), a water-in-oil-in-water emulsion, (W/O/W emulsion), a gel-in-oil-in-gel emulsion (G/O/G emulsion), a gel-in-oil-in water emulsion (G/O/W emulsion), a water-in-oil-in-gel emulsion (W/O/G emulsion) (sic), oil-in-water-in-oil emulsion (O/W/O emulsion), or oil-in-gel-in-oil emulsion (O/G/O emulsion). Also preferred are emulsifiers, which can form an O/W emulsion or W/O emulsion or an O/G emulsion or a G/O emulsion, and which are free of ethylene or propylene glycols or ethylene propylene glycols, that is, they do not contain any substances which containing ethylene, propylene, or ethylene propylene glycol units;

A composition according to the disclosure can have herein in particular about 0.5-50% by weight of at least one emulsifier, especially about 0.5-40% by weight of at least one emulsifier, especially about 0.5-30% by weight of at least one emulsifier, especially about 1-20% by weight of at least one emulsifier, and further yet about 1-10% by weight of at least one emulsifier.

In another form, a composition according to the invention contains thus less than about 10% by weight of water and about 60 to 95% by weight of hydrophilic base, in which about 5-40% by weight of hydrocolloids are dispersed, wherein the hydrophilic base contains about 0.5 to 50% by weight of at least one O/W emulsifier. However, a non-ionic W/O emulsion can also be used instead of the O/W emulsifier.

The advantage when an emulsifier of the O/W type is used is that the complete composition can be washed off especially easily from a wound, for example, by means of water.

It is furthermore preferable to use a composition according to the disclosure containing at least one nonionic emulsifier with an HLB value of from about 3 to 18, according to the definitions listed in the Roempp-Lexikon Chemie, 10th edition, Georg Thieme Publisher Stuttgart, New York, (1997), page 1764. Nonionic O/W emulsifiers with an HLB value of about 10 to about 15 as well as nonionic W/O emulsifiers with an HLB value of about 3 to about 6 are particularly preferred according to the invention.

The emulsifier or emulsifiers, in particular nonionic OW emulsifiers, can advantageously be selected from the group:

Fatty alcohol alkoxylates having the general formula R—O—(CH$_2$—CH$_2$—O)$_n$—H or fatty alcohol propoxylates having the general formula R—O—(CH$_2$—CH(CH$_3$)—O)$_n$—H, wherein R represents a branched or unbranched alkyl or alkenyl group and n represents a number from 10 to 50;

Ethoxylated or propoxylated lanolin alcohols;

Polyethylene glycol ethers having the general formula R—O—(CH$_2$—CH$_2$—O)$_n$—R' polypropylene glycol ethers having the general formula R—O—(CH$_2$—CH(CH$_3$)—O)$_n$—R', wherein R and R' represent, independently from each other, branched or unbranched alkyl or alkenyl groups, and n represents a number from 10 to 80;

Fatty acid ethoxylates having the general formula R—COO—(CH$_2$—CH$_2$—O)$_n$—H or fatty acid propoxylates having the general formula R—COO—(CH$_2$—CH(CH$_3$)—O)$_n$—H, wherein R represents branched or unbranched alkyl or alkenyl groups and n represents a number from 10 to 40;

Etherified fatty acid ethoxylates having the general formula R—COO—(CH$_2$—CH$_2$—O)$_n$—R' or esterified fatty acid propoxylates having the general formula R—COO—(CH$_2$—(CH$_2$—CH(CH$_3$)—O)$_n$—R', wherein R and R' represent, independently from each other, branched or unbranched alkyl or alkenyl groups, and n represents a number from 10 to 80;

Esterified fatty acid ethoxylates having the general formula R—COO—(CH$_2$—CH$_2$—O)$_n$—C(O)—R' or esterified fatty acid propoxylates having the general formula R—COO—(CH$_2$—CH(CH$_3$)—O)$_n$—C(O)—R1, wherein R and R' represent, independently from each other, branched or unbranched alkyl or alkenyl groups, and n represents a number from 10 to 80;

Polyethylene glycol glycerol fatty acid esters or polypropylene glycol glycerol fatty acid esters of saturated and/or unsaturated, branched and/or unbranched fatty acids and a degree of ethoxylation or propoxylation of between 3 and 50;

Ethoxylated or propoxylated sorbitan esters with a degree of ethoxylation or propoxylation of 3 to 100;

Ethoxylated or propoxylated triglycerides with a degree of ethoxylation or propoxylation of 3 to 150;

Polyoxyethylene sorbitol fatty acid esters based on branched or unbranched alkanic or alkenoic acids and featuring a degree of ethoxylation of 5 to 100, for example, of the sorbeth type.

Emulsifiers that can be advantageously utilized within the scope of the invention are, in addition, nonionic W/O emulsifiers from the group of dicarboxylic acid esters or tricarboxylic acid esters. Of these the esters of malonic acid, succinic acid, and adipic acid are particularly suited. Further preferred among these are the esters of dicarboxylic acids, especially the esters of succinic acid, which are formed with saturated or unsaturated and/or linear or branched C8-C24 fatty alcohols and/or glycerin as well as their oligomers, in particular diglycerin or triglycerin. Nonionic W/O emulsifiers of esters of succinic acid with saturated and unsaturated C8-C24 fatty alcohols and/or glycerin as well as their oligomers, in particular diglycerin or triglycerin, have proven to be particularly advantageous. Very particularly suited among these are dicarboxylic acid esters formed from succinic acid and saturated and unsaturated C8-C24 fatty alcohols and diglycerin. Esters of succinic acid with saturated or unsaturated C8-C24 fatty alcohols and/or glycerin as well as their oligomers, in particular diglycerin or triglycerin have proven to be particularly advantageous. Very particularly suited among these are dicarboxylic acid esters formed from succinic acid and saturated and unsaturated C8-C24 fatty acid alcohols and diglycerin. An emulsifier such as this is identified in the INCI nomenclature as isostearyl diglyceryl succinate, and can be obtained under the product name "Imwitor® 780." These emulsifiers have the further advantage that they are polyethylene glycol-free, that is, they do not contain any ethylene glycol units.

In particular ionic O/W emulsifiers can also be used as O/W emulsifiers in connection with the invention. Ionic O/W emulsifiers can particularly be selected as O/W emulsifiers from the group of esters of monoglycerides and/or diglycerides of saturated or unsaturated fatty acids with hydroxycarboxylic acids and/or tricarboxylic acids. Partially neutralized esters of monoglycerides and/or diglycerides of saturated fatty acids with hydroxycarboxylic acids and or tricarboxylic acids, in particular of lactic acid and/or citric acid are particularly preferred as O/W emulsifiers. Esters of lactic acid and/or citric acid, which are called glyceryl cocoates [or] citrates [or] lactates according to the INCI nomenclature, are very particularly preferred. Emulsifiers such as these can be obtained, for example, under the product name "IMWITOR® 380" or "IMWITOR® 377." These emulsifiers have the further advantage that they are polyethylene glycol-free, that is, they do not contain any ethylene glycol units.

According to the present disclosure, a hydrocolloid should be understood to be a material that is a hydrophilic synthetic or natural polymer material, which is soluble or absorbent and/or swells in water and forms a gel. A composition according to the invention preferably contains a hydrocolloid of synthetic or natural polymer material, which is selected from the group of alginic acid and its salts as well as its derivatives, chitin or its derivates, chitosan or its derivatives, pectin, cellulose or its derivatives, such as cellulose ether or cellulose ester, crosslinked or non-crosslinked carboxyalkyl cellulose or hydroxyalkyl cellulose, polyvinyl alcohol, polyvinyl pyrrolidone, agar, guar gum, or gelatin. Cellulose or its derivatives or salts, alginic acid or its derivates or salts, as well as mixtures thereof can be very particularly preferred as hydrocolloid.

The hydrocolloid can be dispersed in the composition both in the form of fibers and in the form of particles and/or fibers. The hydrocolloid can be present in particular in the form of particles. The percentage of hydrocolloid in the composition amounts to 5 to 40% by weight with reference to the overall weight of the composition. The percentage of hydrocolloid can be preferably 5 to 30% by weight, even more preferably 10 to 25% by weight, and very particularly preferably 15 to 25% by weight with reference to the overall weight of the composition.

Hydrocolloids, which are available in particle form, wherein the particles have a water content of less than 10% by weight with reference to the hydrocolloid particles, are particularly preferred.

Hydrocolloids, which are intermolecularly and/or intramolecularly interlaced or crosslinked, are also preferred. These hydrocolloids are not soluble in water or saline solutions, for example, that is, these hydrocolloids swell when these fluids are added and have such an internal cohesion that the particles are dispersed in the composition.

According to another form of the present disclosure, a composition according contains at least one hydrocolloid selected from the group of cellulose derivatives or their salts, alginates or their derivatives, and chitin or its derivatives or salts. The origin of the hydrocolloids is immaterial herein, that is, these hydrocolloids can be of vegetable or animal origin or produced synthetically, for example, by means of microbiological methods. It is also possible to use hydrocolloids which are of vegetable or animal origin and are modified by chemical synthesis.

Cellulose ethers and cellulose esters as well as their salts are particularly included in the group of cellulose derivatives in connection with the invention Hydroxyalkyl celluloses, in particular hydroxy-C1-6-alkyl celluloses, such as, for example, hydroxymethyl cellulose, hydroxyethyl cellulose, hydroxypropyl cellulose, or hydroxybutyl cellulose, and very especially preferred are hydroxymethyl cellulose or hydroxyethyl cellulose are utilized in particular as cellulose ethers. As cellulose esters are particularly used carboxyalkyl cellulose, in particular carboxy-C1-6-alkyl cellulose, such as, for example, carboxymethyl cellulose, carboxyethyl cellulose, carboxypropyl cellulose or carboxybutyl cellulose or their salts, and carboxymethyl cellulose or carboxyethyl cellulose or their salts are very particularly preferred.

According to another form, the composition contains at least two different hydrocolloids. It has proven to be especially advantageous herein when the at least two hydrocolloids are selected from the group of cellulose derivatives or their salts, in particular cellulose esters or their salts, alginates or their derivatives, and chitin or its derivatives or salts.

A wound ointment containing a medicinal composition of the above type is furthermore also an object of the invention. In particular a wound ointment with less than 10% by weight of water containing 60 to 95% by weight of hydrophilic base, in which 5 to 40% by weight of hydrocolloid are dispersed, wherein the hydrophilic base contains 0.5 to 50% by weight of at least one emulsifier, is the object of the invention. This wound ointment can be utilized especially for moderate to hard exuding wounds, since the wound exudate is absorbed to a particular extent by this wound ointment, on the one hand, and a moist environment can be available for the wound by the quantity of hydrocolloids that form a reservoir for fluids, on the other hand. The hydrocolloids act in the wound ointment, at the same time, both as a fluid reservoir and as a moisturizer.

The wound ointment has in one form less than 10% by weight of water and further is 60 to 95% by weight of hydrophilic base, into which 5 to 40% by weight of hydrocolloids are dispersed, wherein the hydrophilic base contains 20-35% by weight of nonpolar fats and 0.5 to 30% by weight of at least one emulsifier. The wound ointment according to the invention very preferably contains, together with less than 10% by weight of water, also 60 to 95% by weight of hydrophilic base, in which 5 to 40% by weight of hydrocolloids are dispersed, wherein the hydrophilic base comprises 50-80% by weight of monoglycerides, diglycerides, triglycerides and/or partial oligomeric glycerol, in particular diglycerin or triglycerin, 20-35% by weight of nonpolar fats, and 0.5-30% by weight of at least one emulsifier. The wound ointment is in particular anhydrous.

The use of a composition with less than 10% by weight of water containing 60 to 95% by weight of hydrophilic base, in which 5 to 40% by weight of hydrocolloids are dispersed, wherein the hydrophilic base comprises 0.5 to 50% by weight of at least one emulsifier, for the production of a medium particularly intended for the production of a wound ointment to treat wounds, in particular to treat burn wounds or chronic wounds, is consequently also an object of the invention.

According to a further concept of the invention, a wound contact layer containing a substrate and a medicinal composition is also an object of the invention. A wound contact layer containing a substrate and a composition with less than 10% by weight of water containing 60 to 95% by weight of hydrophilic base, in which 5 to 40% by weight of hydrocolloids have been dispersed, wherein the hydrophilic base contains 0.5 to 50% by weight of at least one emulsifier, is a particular object of the invention. The substrate ensures that the wound contact layer maintains an easily applicable shape, which can be applied directly and over the entire surface of a wound. The composition can also be applied over at least one side of the substrate or in another manner. The composition can also be applied on both sides of the substrate or the substrate can be entirely impregnated with the composition.

A further advantage with respect to known wound contact layers is that, when it is applied on a wound, which normally is carried out by trained personnel by means of gloves, a wound contact layer according to the invention does not adhere or stick to the gloves. These wound contact layers are thus especially safe to handle.

The wound contact layer has particularly a substrate and a composition with less than 10% by weight of water, wherein the composition contains 60 to 95% by weight of hydrophilic base, in which 5 to 40% by weight of hydrocolloids are dispersed, and wherein the hydrophilic base contains 20-35% by weight of nonpolar fats and 0.5-30% by weight of at least one emulsifier. The wound contact layer according to the invention contains particularly preferably a substrate and a composition with less than 10% by weight of water, wherein the composition contains 60 to 95% by weight of hydrophilic base, in which 5 to 40% by weight of hydrocolloids are dispersed, and wherein the hydrophilic base contains 50-80% by weight of monoglycerides, diglycerides, triglycerides and/or partial esters of oligomeric glycerol, in particular diglycerin or triglycerin, 20-35% by weight of nonpolar fats, and 0.5-30% by weight of at least one emulsifier. The composition is particularly anhydrous.

The portion of fatty acid glycerides in the composition makes available therapeutic components to the skin surrounding a wound, the so-called peripheral wound skin, which particularly promotes wound healing.

Various materials can be used as substrate herein. It has in particular been discovered that polymer films or foils, polymer foams, and nonwoven as well as textile materials can be used for this purpose. The substrate in a wound contact layer according to the invention can be nonwoven as well as textile materials, such as knitted, crocheted, or woven materials. Hydrophobic knitted, crocheted, or woven materials can be very particularly preferably used, which do not absorb fluids of themselves. A wound contact layer according to the invention contains in particular a polyamide crocheted layer as substrate.

If a textile substrate is used, the material can in particular also be provided with openings, that is, the substrate is supplied with holes or is made available in lattice form. The substrate can be in particular a crocheted, woven, or knitted material with holes, whose maximal inner width is within the range of 0.3 to 3.0 mm, preferably 0.5 to 2.5 mm, and especially preferably from 0.5 to 2.0 mm when the material is not stretched. The holes can assume any shape herein, such as, for example, circular, elliptical, quadratic, hexagonal, or octagonal. These crocheted materials feature a weight per unit area of at least 20 g/m2 up to at the most 120 g/m2.

At least one substance that promotes wound healing can be furthermore released through the wound contact layer. To these belong in particular substances having fungicidal, bactericidal, or antimicrobial effects. In a special embodiment, the wound contact layer contains a hydrocolloid, which contains, in turn, at least one fungicidal, bactericidal, or antimicrobial substance. Very particularly suited for this are chitosan, silver, silver complexes, silver salts, zinc, zinc salts, or zinc complexes.

A wound-healing promoting agent can also be applied directly on the substrate. In a further embodiment of the wound contact layer, a nonwoven or a textile material, such as a knitted, crocheted, or woven material is used as substrate in a particularly advantageous manner, and is coated with an antimicrobial metal, preferably silver or silver salts. When such a substrate is used, the composition can be applied directly on the metal or metal salt on a first side of the substrate. It is particularly advantageous herein if the composition is anhydrous.

The antimicrobial metal can also be applied as a coating on the substrate or is impregnated or incorporated on or in the carrier. Here can be used in particular silver, silver salts, or silver complexes as antimicrobial metal.

It can be furthermore provided that the wound contact layer contains a nonwoven material as substrate, which consists of a fiber mixture of fibers containing antimicrobial metal and metal-free fibers.

According to another form, the substrate can consist of multiple layers. In this case, only one of the layers of the substrate can have an antimicrobial metal, which can be released by means of the wound contact layer. As an alternative, antimicrobial metals of the same or different type can be stored in several layers.

It can be provided that in particular the wound contact layer releases less than 500 μg/100 cm2 of antimicrobial metal in 24 h at 37° C. in 100 ml of water, in particular less than 400 μg/100 cm2 in 24 h at 37° C. in 100 ml of water, and especially less than 300 μg/100 cm2 in 24 h at 37° C. in 100 ml of water. However, it can be particularly provided that the wound contact layer releases more than 2 μg/100 cm2 in 24 h at 37° C. in 100 ml of water. Atomic absorption spectroscopy is utilized for the determination of the released quantity of silver.

The fact that the substrate contains a composition on at least its first side should be understood to mean according to the invention that the composition is arranged either directly on the carrier supplied with the metal, or that first a continuous or discontinuous metal layer is applied to the first side, on which the composition is then applied. A bilateral application of the composition can also be desired, in particular when tamponing of the wound dressing should be provided. In this case, it is advantageous to apply the metal application on both sides or to enclose the crocheted material in the carrier.

The composition, which can be in particular an ointment or cream, acts herein as the intermediary between the substrate provided with the metal and the wound of the patient. In this manner, a direct contact of the wound with the metal and in particular also an adhesion with it can be securely prevented. This ointment or cream can also produce a therapeutic effect in the region of the peripheral wound skin. If the wound contact layer does come into contact with the wound by means of the composition, the metal, for example, silver, is released from the wound dressing under the influence of the composition, in particular via the wound exudate, and said metal reaches the wound via the composition. Elemental silver can be particularly used as the metal. The metal can be disposed as a layer on the substrate or can be impregnated in the carrier.

Particularly advantageous is an application of a composition, in particular an ointment, cream, or cream base, on a substrate in a quantity of at least 50 g/m2, especially of at least 100 g/m2, especially preferably of 100 to 450 g/m2, and very particularly preferably, of 100 to 300 g/m2.

The present disclosure further comprises a wound dressing containing a cover layer and a wound contact layer. The wound contact layer contains herein a composition or a wound ointment containing a hydrophilic base, in which hydrocolloids are dispersed, where the hydrophilic base contains at least one emulsifier. The invention comprises in particular a wound dressing consisting of a cover layer and a wound contact layer, wherein the wound contact layer contains a composition with less than 10% by weight of water having 60 to 95% by weight of hydrophilic base, in which 5 to 40% by weight of hydrocolloids are dispersed, wherein the hydrophilic base contains 0.5 to 50% by weight of at least one emulsifier.

The invention comprises in particular a wound dressing having a cover layer and a wound contact layer, wherein the wound contact layer comprises a substrate and a composition with less than 10% by weight of water, which further contains 60 to 95% by weight of hydrophilic base, in which 5 to 40% by weight of hydrocolloids are dispersed, wherein the hydrophilic base contains 0.5 to 50% by weight of at least one emulsifier.

According to a further development of the disclosure, the invention also comprises a wound dressing having a cover layer, an absorbent layer, and a wound contact layer, wherein the wound contact layer contains a composition with less than 10% by weight of water containing 60 to 95% by weight of hydrophilic base with 0.5 to 50% by weight of at least one emulsifier, in which 5 to 40% by weight of hydrocolloids are dispersed.

As cover layer, the wound dressing can have in particular a polymer foil or a polymer film. Very particularly preferred are polymer films having high water vapor permeability. Polyurethane, polyether urethane, polyester urethane, polyether-polyamide copolymers, polyacrylate or polymethacrylate films are especially suited for this purpose. In particular polyurethane film, polyester urethane film, or polyether urethane film is preferred as a polymer film. Also very particularly preferred, however, are polymer films having a thickness of 15 to 50 μm, in particular 20 to 40 μm, and very particularly preferably 25 to 30 μm. The water vapor permeability of the polymer film of the wound dressing is preferably at least 750 g/m2/24 h, in particular at least 1000 g/m2/24 h, and very particularly preferably at least 2000 g/m2/24 h (measured in accordance with DIN 13726).

A wound dressing according to the disclosure can also be made available as a so-called island dressing. The wound contact layer has herein a smaller dressing surface than the cover layer, that is, the wound contact layer is surrounded by a cover layer along its periphery. The cover layer can have herein an adhesive agent or be made to be adhesive, so that the entire wound dressing can stick or adhere to the skin of the patient. This application of the adhesive can be continuous or also discontinuous, or only be provided in specific areas. The utilized adhesive can be a normal adhesive, in particular an acrylate adhesive or pressure-sensitive adhesive based on polyurethane. It is preferably a gel adhesive, based in particular on polyurethanes, in particular aqueous polyurethanes. Very particularly preferred is a hydrogel adhesive, based in particular on aqueous acrylates.

According to a further development, the wound dressing can have a cover layer, which is coated over its entire surface with adhesive agent. The water vapor permeability of this carrier layer provided with the adhesive amounts herein preferably to at least 1000 g/m2/24 h, particularly preferably to at least 1200 g/m2/24 h, and very particularly preferably to at least 2000 g/m224 h (measured in accordance with DIN EN 13726).

A wound dressing according to the disclosure can be available in any geometric form, for example triangular, round, oval or quadratic, rectangular, or can have any symmetrical or asymmetrical shape.

A wound dressing according to the disclosure can also have additional layers, which can possess different functions. According to one further development of the invention, the wound dressing has at least one additional layer. This layer can be preferably a release layer for protection against contamination, which is applied on the side of the wound contact layer that is to be placed on the wound when the dressing is ready for use. The wound dressing can also have at least one further layer between the wound contact layer and the cover layer. This additional layer can be an absorbent layer, such as, for example, an absorbent layer of hydrophilic foam material, such as, for example, polyurethane.

The use of a composition with less than 10% by weight of water containing 60 to 95% by weight of hydrophilic base, in which 5 to 40% by weight of hydrocolloids are dispersed, wherein the hydrophilic base contains 0.5 to 50% by weight of at least one emulsifier, for the production of a wound contact layer or a wound dressing in particular for the treatment of burn wounds or chronic wounds, is thus also an object of the invention.

In another form of the disclosure, it is provided that a wound dressing according to the invention is disposed in a package. It is provided in particular that the package is a sterile package. In another special embodiment of the invention, it is provided that a system comprising a wound contact layer of the described type and a separate wound dressing is disposed in a package. In a particularly preferred embodiment of this system, each separate component is placed in the package or sterile package or each group of components are each placed separately in separate package within the package. It can also be provided that a separate package is a sterile separate package.

It must be emphasized at this point that the features of the alternative embodiments of the invention cited herein should not be limited to the individual alternatives. It is rather the case that the combination of embodiments or the combination of individual features of the alternative embodiments can likewise be considered an embodiment according to the invention. The invention should also likewise not be considered limited in any way by the following description of the drawings.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figure 2:
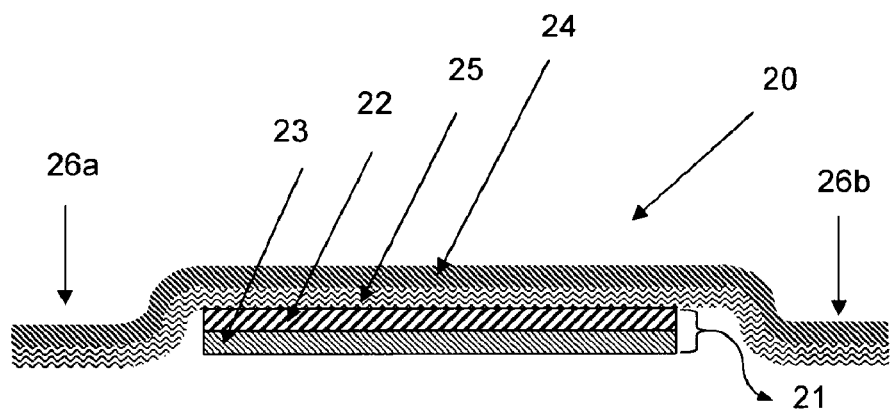

The invention will be described in the following with reference to the drawings and the examples, wherein:

FIG. 1: shows a cross section of the wound contact layer;
FIG. 2: shows a cross section of the wound dressing; and
FIG. 3: shows a cross section of an alternative wound dressing.

DETAILED DESCRIPTION

The following description is merely exemplary in nature and is not intended to limit the present disclosure, application, or uses.

Examples

Composition 1

| No. | Brand Name | Name - INCI, Function | Content % by weight |
|---|---|---|---|
| 1 | IMWITOR 780 K (Sasol, Witten - Germany) | Isostearyl diglyceryl succinate, nonionic W/O-emulsifier HLB 3.7 | 5.0 |
| 2 | IMWITOR 780 K (Sasol, Witten - Germany) | Glyceryl stearate, coemulsifier | 4.0 |

-continued

| No. | Brand Name | Name - INCI, Function | Content % by weight |
|---|---|---|---|
| 3 | SOFTISAN 100 (Sasol, Witten - Germany) | Hydrogenated cocoglycerides, polar fat | 4.0 |
| 4 | SOFTISAN 378 (Sasol, Witten - Germany) | Caprylic/capric/myristic/ stearic triglycerides, polar fat | 23.0 |
| 5 | SOFTISAN 649 (Sasol, Witten - Germany) | Bis-diglyceryl polyacyladipate-2, polar fat | 19.0 |
| 6 | MERKUR Vaseline 115 (Merkur Vaseline GmbH & Co. KG, Hamburg, Germany) | Petrolatum, nonpolar lipid | 25.0 |
| 7 | Bianose 7H3SXF (Herkules - Germany) | Cellulose gum, sodium carboxymethyl cellulose, hydrocolloid | 20.0 |

Production of Composition 1: Phase A (components 1 through 6) is melted and stirred at approximately 75-80° C.

Phase B (component 7) is then dispersed in phase A under energetic stirring. The ointment compound is cooled under energetic stirring, so that a fine crystal structure is produced. The dripping point of the composition amounts to 46° C. (determined according to Ph. Eur. 2002, Method 2.2.17)

2) Composition 2

| No. | Brand Name | Name - INCI, Function | Content, % by weight |
|---|---|---|---|
| 1 | IMWITOR 377 K (Sasol, Witten - Germany) | Glyceryl laurates citrates, ionic O/W emulsifier | 5.0 |
| 2 | IMWITOR 900 K (Sasol, Witten - Germany) | Glyceryl stearate, coemulsifier | 4.0 |
| 3 | SOFTISAN 100 (Sasol, Witten - Germany) | Hydrogenated cocoglycerides, polar fat | 4.0 |
| 4 | SOFTISAN 378 (Sasol, Witten - Germany) | Caprylic/capric/myristic/ stearic triglycerides, polar fat | 23.0 |
| 5 | SOFTISAN 649 (Sasol, Witten - Germany) | Bis-diglyceryl polyacyladipate-2, polar fat | 19.0 |
| 6 | MERKUR Vaseline 115 (Merkur Vaseline GmbH & Co. KG, Hamburg, Germany) | Petrolatum, nonpolar lipid | 25.0 |
| 7 | Bianose 7H3SXF (Herkules - Germany) | Cellulose gum, sodium carboxymethyl cellulose, hydrocolloid | 20.0 |

Production of Composition 2:

Phase A (components 1 through 6) is melted and stirred at approximately 75-80° C.

Phase B (component 7) is then dispersed in phase A under energetic stirring. The ointment compound is cooled under energetic stirring, so that a fine crystal structure is produced. The dripping point of the composition amounts to 48° C. (determined according to Ph. Eur. 2002, Method 2.2.17).

3) Wound Contact Layer 1

The wound contact layer has the structure shown in FIG. 1. Accordingly, the wound contact layer (10) has a substrate (1), which is coated on both sides or surfaces with a composition (2a and 2b) according to example 1. The substrate (1) consists of a polyamide crocheted substrate coated with elemental silver, which is produced with nylon 6 trilobal threads with 50 μm edge length. The raw material (without silvering) has a weight per unit area of between 25 and 30 g/m2 and a thread count of dtex=22/1. In the material, there are between 11,360 and 13,640 m threads per square meter. This means that the surface amounts to between 1.7 m2 and 2.04 m2. The layer thickness of the silver on the substrate amounts to approximately 700 nm. There is no detectable difference between the silvered and unsilvered product with conventional means (light microscope) in the triangular side length. The weight per unit area of the silvered crocheted piece is approximately 35±3 g/m2. Here the content of elemental silver is around 130 mg/g of polyamide crocheted substrate. Silver-coated crocheted materials such as these are made by the Statex company, Bremen, under the name Shieldex® Tulle Type Charmeuse, and were used herein as substrate. The composition fully coats the substrate, wherein the applied quantity is 280 g/m2. The wound contact layer has a good cohesion and can be applied especially well to a wound to be treated;

4) Wound Contact Layer 2 (not According to the Invention)

This wound contact layer also has a structure shown in FIG. 1. This wound contact layer (10) has the composition with the components indicated in Example 1. The substrate (1) consists of a hydrophobic 100% polyamide crocheted material (Theodor Preuss GmbH & Co., KG, Ubstadt-Weiher—Germany) with a weight per unit area of around 90 g/m$^2$ (unstretched) and has approximately 46 hexagonal openings per 100 cm (not shown in FIG. 1). The maximum inner width of the openings is 0.8-1.0 mm. The application weight of the composition is 240 g/m$^2$. The coating of the textile substrate with the hydrophilic composition is carried out by guiding the substrate via a guide roller through a warm reservoir bath (40° C.) of hydrophilic composition 1. After passing through the bath, the excess amount of transferred composition is stripped off by means of a squeegee. The coated material is brought to room temperature, assembled, packaged and sterilized.

5) Wound Contact Layer 3 (not according to the invention). This wound contact layer also has a structure as in FIG. 1. In this wound contact layer (10), the composition has the components indicated in Example 2. The substrate (1) consists of a hydrophobic 100% polyamide crocheted material (Theodor Preuss GmbH & Co. KG, Ubstadt-Weiher—Germany) with a weight per unit area of approximately 80 g/m$^2$ (unstretched) and has approximately 40 hexagonal openings per 100 cm (not shown in FIG. 1). The maximum inner width of the openings is 1.2-1.5 mm. The application weight of the substrate is approximately 330 g/m$^2$.

The textile substrate is coated with hydrophilic composition by running the substrate via a guide roller into a warm bath (60° C.) of the hydrophilic composition 2. After passing through the bath, the excess amount of transferred composition is stripped off by means of a squeegee. The coated material is brought to room temperature, assembled, packaged, and sterilized.

Measurement of the water absorption of the wound contact layers according to the invention in comparison with commercially available products in a simulated wound environment:

The background of this test consists in obtaining evidence concerning how a wound contact layer behaves on a wound, for example, a moderately exuding or highly exuding wound.

a) The gelatin solution is produced as follows:

i) Production of Solution A: 0.277 g of calcium chloride and 8.298 g of sodium chloride are placed in a graduated one-liter cylinder at room temperature and the latter is filled up to 1 liter with deionized water. The solution is stirred until the salts are dissolved.

ii) Production of the Gelatin Solutions×g of gelatin powder (type A from pigskin, 175 Bloom, GELITA gelatin, DGF Stoess AG, 69402 Eberbach) are added to y g of the above solution A at room temperature in order to produce an x % gelatin solution. The gelatin is added all at once and quickly to the solution A, the solution is energetically shaken, so that all the particles are wetted with the solution, and the resulting mixture is stirred in the water bath at 60☐ C. for 24 hours. Care must be taken that no water escapes. 20% (x=20, y=8) and 35% (x=35, y=65) gelatin solutions are made in this way.

b) After 24 hours, Petri dishes with a diameter of 9 cm are filled with 30 g of the gelatin solution, which his still warm, closed with the appropriate cover, and cooled to room temperature. The resulting solid gels are used for the analysis of the test pieces.

c) In order to analyze the wound contact layer according to the invention, 3×3 cm pieces are analyzed by placing these test pieces with one side over the entire surface of Petri dishes filled with gelatin solution, after which the Petri dishes are closed with their covers and allowed to stand at room temperature for 24 hours. After 24 hours, the absorbed quantity of liquid is determined by weighing the test pieces. Care must be taken herein that the weight of the test pieces is determined as a whole. If necessary, a remnant remaining on the gelatin surface must be carefully removed with a suitable scraper and included in the weighing. The results are shown in Table 1 and Table 2, wherein three measurements were carried out for each specimen, and each test piece was placed in a separate Petri dish.

For analysis were available:

Specimen 1: wound contact layer of example 4, sterilized by beta radiation (40 kGy);

Specimen 2: wound contact layer of example 5, sterilized by beta radiation (40 kGy);

Specimen 3: Urgotül®, Urgo Co.; and

Specimen 4: Physiotulle®, Coloplast Co.

TABLE 1

Testing on a 20% Gelatin Solution

| Specimen | Input weight of specimen | Output weight of specimen after 24 h/g | Water absorption after 24 h/g | Water absorption after 24 h (based on input weight) Individual values | Average values |
|---|---|---|---|---|---|
| 1 | 0.320 | 0.698 | 0.378 | 118% | 125% |
|   | 0.310 | 0.709 | 0.399 | 129% |   |
|   | 0.320 | 0.726 | 0.406 | 127% |   |
| 2 | 0.410 | 1.054 | 0.644 | 157% | 158% |
|   | 0.500 | 1.283 | 0.783 | 157% |   |
|   | 0.430 | 1.115 | 0.685 | 159% |   |
| 3 | 0.190 | 0.224 | 0.034 | 18% | 15% |
|   | 0.194 | 0.219 | 0.025 | 13% |   |
|   | 0.200 | 0.226 | 0.252 | 13% |   |
| 4 | 0.243 | 0.330 | 0.087 | 36% | 36% |
|   | 0.231 | 0.320 | 0.088 | 38% |   |
|   | 0.235 | 0.315 | 0.080 | 34% |   |

TABLE 2

Testing on a 35% Gelatin Solution

| Specimen | Input weight | Output weight after 24 h/g | Water absorption after 24 h/g | Water absorption after 24 h (based on input weight) Individual values | Average values |
|---|---|---|---|---|---|
| 1 | 0.308 | 0.577 | 0.269 | 85% | 91% |
|   | 0.318 | 0.575 | 0.257 | 81%# |   |
|   | 0.313 | 0.615 | 0.302 | 96% |   |

TABLE 2-continued

Testing on a 35% Gelatin Solution

| Specimen | Input weight | Output weight after 24 h/g | Water absorption after 24 h/g | Water absorption after 24 h (based on input weight) Individual values | Average values |
|---|---|---|---|---|---|
| 2 | 0.496 | 1.069 | 0.573 | 116% | 115% |
|  | 0.441 | 0.950 | 0.509 | 115% |  |
|  | 0.449 | 0.965 | 0.516 | 115% |  |
| 3 | 0.189 | 0.226 | 0.037 | 19% | 18% |
|  | 0.190 | 0.225 | 0.035 | 18% |  |
|  | 0.192 | 0.227 | 0.035 | 18% |  |
| 4 | 0.227 | 0.281 | 0.054 | 24% | 25% |
|  | 0.237 | 0.296 | 0.059 | 25% |  |
|  | 0.238 | 0.297 | 0.059 | 25% |  |

Test piece not fully flat on the gelatin surface (not counted).

The results of Table 1 represent an approximation of the behavior of the wound contact layers on moderately to heavily exuding wounds. According to this, a wound contact layer according to example 5 (specimen 2) absorbs an average of 158% times its own weight in liquid in 24 hours. In comparison with this, a commercially available shows much lower moisture absorption. The values were an average for specimen 4 of 36% and for specimen 3 of 15%. A similar trend can be demonstrated with the results in Table 2. This examination represents a simulation of a weak to moderately heavily exuding wound. According to it, a wound contact layer according to example 5 (specimen 2) in 24 h absorbs an average of 115% of its own weight in liquid. In comparison with this, the commercially available products show a much lower moisture absorption capacity. The values on average for specimen 4 were at 25% and for specimen 3 at 19%. If the results of the two tests are compared to each other, it can further be determined that the wound contact layer also demonstrates a need-based moisture absorption, which means that more moisture is absorbed with strongly exuding wounds than in rather moderately exuding wounds.

6) Wound Dressing 1.

A wound dressing (20) according to the invention is shown as a so-called island dressing in FIG. 2. The wound dressing consists of a cover layer (24) and a wound contact layer (21). The wound contact layer consists, in turn, of a substrate (22), which is a hydrophobic nonwoven of polyester fibers, coated with a composition (23) in accordance with example 1, wherein part of the polyester fibers are coated with elemental silver. With an application quantity of 240 g/m², the composition fully covers the polyester nonwoven (water jet reinforced, weight per unit area of 80 g/m²). The wound contact layer is covered with a cover layer (24), which is coated with a polyacrylate adhesive (25) over its entire surface. The cover layer is a 30 μm thick polyurethane film with a water vapor permeability of 1100 g/m²$^{/24}$ h extending to all sides beyond the periphery of the wound contact layer, so that the wound contact layer can be attached to the skin of the patient by means of the adhesive edges of the cover layer (26a, 26b). At the same time, the wound contact layer (22) is fixed on the cover layer by means of the adhesive (25).

7) Wound Dressing 2.

Figure 3:
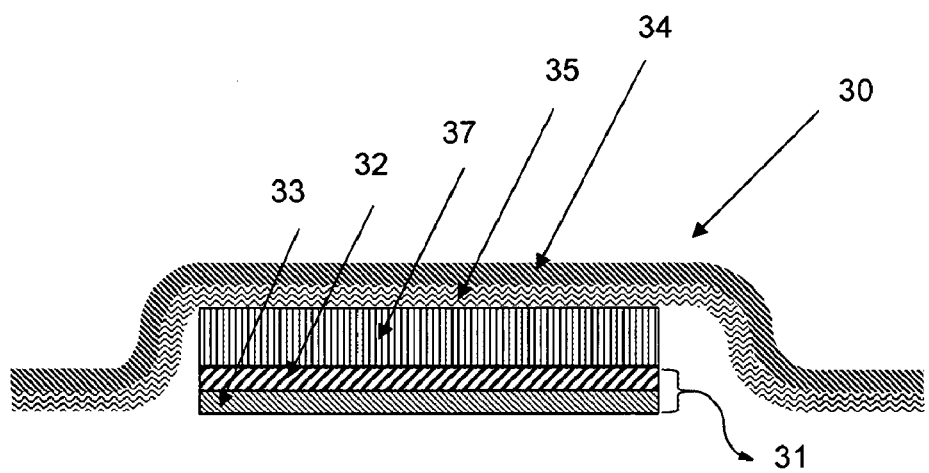

FIG. 3 shows a further wound dressing (30) according to the invention, which in comparison with the wound dressing (20) shown in FIG. 2 has an additional absorbent layer (37). This additional absorbent layer (37) consists of hydrophilic open celled polyurethane foam with a weight per area of 500 g/m² and a thickness of 5 mm. The absorbent layer is affixed on the cover layer by means of the adhesive layer (35) made from an acrylate dispersion adhesive. The cover layer consists of a polyurethane film with a thickness of 25 μm and a water permeability of 1200 g/m²$^{/24}$ h. The wound contact layer (31) consists of a substrate (32), which is coated on the side facing the wound or its surfaces with a composition in accordance with example 2 (180 g/m²). The substrate (1) consists of a polyamide carrier crocheted material coated with elemental silver and produced from Nylon 6 trilobal thread with 50 μm edge length. The raw material (without silvering) has a weight per unit area of 25 to 30 g/m² and a thread count of dtex=22/1. In the material, between 11,360 and 13,640 m of thread are worked into one square meter. This means that the surface amounts to between 1.7 m² and 2.04 m². The layer thickness of the silver on the substrate amounts to approximately 700 nm. There is no detectable difference between the silvered and unsilvered product using conventional means (light microscope) in the triangular side length. The weight per unit area of the silvered crocheted material is 35±3 g/m². The content of elemental silver is herein approximately 130 mg/g of polyamide crocheted carrier. Silver-coated crocheted material such as these are sold by the Statex company, Bremen, under the name Shieldex® Tulle Type Charmeuse and were used herein as substrate. The wound dressing is especially suited for use with heavily exuding wounds. The wound dressing nurtures the peripheral wound skin due to its portion of triglycerides in the composition and does not stick to the wound also during long periods of use.

It should be noted that the disclosure is not limited to the embodiment described and illustrated as examples. A large variety of modifications have been described and more are part of the knowledge of the person skilled in the art. These and further modifications as well as any replacement by technical equivalents may be added to the description and figures, without leaving the scope of the protection of the disclosure and of the present patent.

What is claimed is:

1. A wound contact layer comprising:
   a) a composition for wound treatment containing 60 to 95% by weight of hydrophilic base, in which 5 to 40% by weight of hydrocolloids have been dispersed, wherein the hydrophilic base contains
      about 0.5 to about 50% by weight of at least one emulsifier
      20 to 80% by weight of monoglycerides, diglycerides, or triglycerides and/or full or partial esters of oligomeric glycerol,
      10 to 30% by weight of nonpolar lipids, and
      up to 1% by weight of water; and
   b) a substrate for the composition containing a metal with antimicrobial action.

2. The wound contact layer according to claim 1, characterized in that the hydrophilic base contains Icon than 10% by weight of water or is anhydrous.

3. The wound contact layer according to claim 1, characterized in that the hydrophilic base cream, cream base, and an ointment.

4. The wound contact layer according to claim 1, characterized in that the hydrocolloids are in particle form.

5. The wound contact layer according to claim 1, characterized in that the hydrocolloids are selected from the group consisting of cellulose or their derivatives or salts, and alginic acid or its derivatives or salts.

6. The wound contact layer according to claim 1, characterized in that the emulsifier is an ionic oil in water emulsifier.

7. The wound contact layer according to claim 1, characterized in that the emulsifier is a nonionic water in oil emulsifier.

8. The wound contact layer according to claim 1, characterized in that the substrate is selected from the group consisting of a nonwoven, knitted, crocheted, and a woven material.

9. The wound contact layer according to claim 1, characterized in that that the metal is applied as a coating on the substrate.

10. The wound contact layer according to claim 1, characterized in that that the metal is impregnated or incorporated in or on the substrate.

11. The wound contact layer according to claim 1, characterized in that the substrate is a nonwoven material having a fiber mixture of fibers containing an antimicrobial metal and metal-free fibers.

12. The wound contact layer according to claim 1, characterized in that the substrate is selected from the group consisting of hydrophobic knitted, crocheted, and woven material.

13. The wound contact layer according to claim 1, characterized in that the substrate comprises a crocheted polyamide material.

14. The wound contact layer according to claim 1, characterized in that the antimicrobial metal is selected from the group consisting of an elemental silver, a silver salt, and a silver complex.

15. The wound contact layer according to claim 1 further comprising a cover layer.

16. The wound contact layer according to claim 15, further comprising an absorbent layer, which is adjacent to the wound contact layer.

17. The wound contact layer according to claim 1, wherein the nonpolar lipids are selected from the group consisting of petroleum jelly, petrolatum, paraffin oil, and wax.

18. The wound contact layer according to claim 1, wherein the substrate is selected from the group consisting of a nonwoven, knitted, crocheted, and woven material, and the substrate is coated with an antimicrobial metal.

* * * * *